(12) United States Patent
Boppana et al.

(10) Patent No.: US 9,828,322 B2
(45) Date of Patent: *Nov. 28, 2017

(54) EFFICIENT SYNTHESIS OF METHACROELIN AND OTHER ALPHA, BETA-UNSATURATED ALDEHYDES OVER A REGENERABLE ANATASE TITANIA CATALYST

(71) Applicant: EASTMAN CHEMICAL COMPANY, Kingsport, TN (US)

(72) Inventors: Venkata Bharat Boppana, Johnson City, TN (US); David William Norman, Kingsport, TN (US); Gerald C. Tustin, Kingsport, TN (US); Melissa Page Steffey, Nickelsville, VA (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,721

(22) Filed: Jan. 28, 2016

(65) Prior Publication Data
US 2017/0217867 A1   Aug. 3, 2017

(51) Int. Cl.
*C07C 45/72* (2006.01)
*C07C 45/75* (2006.01)
*B01J 21/06* (2006.01)

(52) U.S. Cl.
CPC ............. *C07C 45/75* (2013.01); *B01J 21/063* (2013.01)

(58) Field of Classification Search
CPC ................................ C07C 45/38; C07C 45/72
USPC .......................................... 568/463, 464, 473
See application file for complete search history.

(56) References Cited

U.S. PATENT DOCUMENTS

| | | |
|---|---|---|
| 2,111,584 A | 3/1938 | Eversole |
| 2,462,413 A | 2/1949 | Meath |
| 2,639,295 A | 5/1953 | Hagemeyer, Jr. et al. |
| 2,953,602 A * | 9/1960 | Aries ..................... C07C 45/49 568/487 |
| 3,574,703 A | 4/1971 | Hagemeyer, Jr. et al. |
| 3,701,798 A | 10/1972 | Snapp et al. |
| 3,845,106 A | 10/1974 | Hagemeyer, Jr. et al. |
| 3,928,458 A | 12/1975 | Hatemeyer, Jr. et al. |
| 3,959,383 A | 5/1976 | Northeimer |
| 4,101,586 A | 7/1978 | Deem et al. |
| 4,283,564 A | 8/1981 | Bernhagen et al. |
| 4,316,990 A * | 2/1982 | Morris ..................... C07C 45/74 568/461 |
| 4,408,079 A | 10/1983 | Merger et al. |
| 4,433,174 A | 2/1984 | Hagen |
| 4,496,770 A * | 1/1985 | Duembgen ............. C07C 45/75 568/463 |
| 4,528,405 A | 7/1985 | Papa |
| 4,943,663 A | 7/1990 | Diekhaus et al. |
| 5,777,183 A | 7/1998 | Mueller et al. |
| 5,990,358 A | 11/1999 | Knuth et al. |
| 6,147,263 A * | 11/2000 | Wachs ..................... C07C 45/00 568/473 |
| 6,419,797 B1 | 7/2002 | Scherf et al. |
| 7,012,156 B2 | 3/2006 | Lee et al. |
| 7,501,546 B2 | 3/2009 | Koivusalmi et al. |
| 7,663,006 B2 | 2/2010 | Oota et al. |
| 7,700,810 B2 | 4/2010 | Kourtakis et al. |
| 7,700,811 B2 | 4/2010 | Kourtakis et al. |
| 7,732,644 B2 | 6/2010 | Ishida et al. |
| 7,977,517 B2 | 7/2011 | Cortright et al. |
| 8,048,290 B2 | 11/2011 | Knuuttila et al. |
| 8,080,695 B2 | 12/2011 | Tsuchida et al. |
| 8,143,469 B2 | 3/2012 | Koivusalmi et al. |
| 8,187,347 B2 | 5/2012 | Sakuma et al. |
| 2010/0286455 A1 | 11/2010 | Ozer et al. |
| 2010/0298614 A1 | 11/2010 | Ozer et al. |
| 2011/0021845 A1 | 1/2011 | Zim et al. |
| 2011/0245554 A1 | 10/2011 | Huber et al. |
| 2012/0144733 A1 | 6/2012 | Truitt |

(Continued)

FOREIGN PATENT DOCUMENTS

| | | |
|---|---|---|
| CN | 101074192 A | 11/2007 |
| CN | 101659597 | 3/2010 |
| DE | 10232458 | 7/2003 |

(Continued)

OTHER PUBLICATIONS

Co-pending U.S. Appl. No. 15/008,833, filed Jan. 28, 2016; Boppana et al.
Office Action dated Jul. 5, 2016 received in co-pending U.S. Appl. No. 15/008,833.
Office Action dated Jan. 26, 2017 received in co-pending U.S. Appl. No. 15/008,833.
Nagai, Koichi; "New developments in the production of methyl methacrylate"; Applied Catalysis A: General; 221; 2001; pp. 367-377.

(Continued)

*Primary Examiner* — Sikarl Witherspoon
(74) *Attorney, Agent, or Firm* — Dennis V. Carmen

(57) ABSTRACT

A commercially available anatase titania catalyst is shown to be catalytically active towards the formation of methacrolein from formaldehyde and propionaldehyde with conversions and selectivities close to 90%. This titania catalyst is readily available, non-toxic, and can be used with formaldehyde and a variety of other aldehyde compounds to make α,β-unsaturated aldehyde compounds. This process benefits from low raw material costs and is economically advantaged due to the elimination of catalyst separation. An additional advantage of this method involves the ability of the catalyst to be fully regenerated after a calcination step at 450° C. in air. This process shows promising stability and selectivity during lifetime studies, particularly when performed in the presence of a hydrogen carrier gas.

18 Claims, 1 Drawing Sheet

(56) References Cited

U.S. PATENT DOCUMENTS

2012/0157732 A1 6/2012 Truitt
2012/0283479 A1 11/2012 Dubois

FOREIGN PATENT DOCUMENTS

| EP | 0440420 | | 7/1991 |
|---|---|---|---|
| GB | 513772 | A | 10/1939 |
| JP | 61059612 | B | 3/1982 |
| JP | 04173760 | A | 6/1992 |
| JP | 05000990 | A | 1/1993 |
| JP | 08259487 | A | 10/1996 |
| JP | 2908591 | B2 | 6/1999 |
| JP | 2922673 | B2 | 7/1999 |
| JP | 2925781 | B2 | 7/1999 |
| JP | 4306559 | B2 | 8/2009 |
| JP | 4306662 | B2 | 8/2009 |

OTHER PUBLICATIONS

Zhang et al.; "Preparation and Characterization of Nanosized $TiO_2$ Powders from Aqueous $TiCl_4$ Solution"; NanoStructured Materials; vol. 11; No. 8; 1999; pp. 1293-1300.

Zhang et al.; "Preparing Single-Phase Nanocrystalline Anatase from Amorphous titania with Particle Sizes Tailored by Temperature"; Nano Letters; 2001; vol. 1; No. 2; pp. 81-85.

Yanagisawa et al.; "Crystallization of Anatase from Amorphous Titania Using the Hydrothermal Technique: Effects of Starting Material and Temperature"; J. Phys. Chem. B; 1999; 103; pp. 7781-7787.

Carlini et al.; "Guerbet condensation of methanol with n-propanol to isobutyl alcohol over heterogeneous copper chromite/Mg—Al mixed oxides catalysts"; Journal of Molecular Catalysis A: Chemical, 220; 2004; pp. 215-220.

Carlini et al.; "Selective synthesis of 2-ethyl-1-hexanol from n-butanol through the Guerbet reaction by using bifunctional catalysts based on copper or palladium precursors and sodium butoxide"; Journal of Molecular Catalysis A: Chemical; 2012; 2004; pp. 65-70.

Carlini et al.; "Selective synthesis of Isobutanol by means of the Guerbet reaction Part 2. Reaction of methanol/ethanol and methanol/ethanol/n-propanol mixtures over copper based MeONa catalytic systems"; Journal of Molecular Catalysis A: Chemical; 200; 2003; pp. 137-146.

Carlini et al.; "Synthesis of Isobutanol by the Guerbet condensation of methanol with n-propanol in the presence of heterogeneous and homogeneous palladium-based catalytic systems"; Journal of Molecular Catalysis A: Chemical; 204-205; 2003; pp. 721-728.

Guerbet, M.; "Action of ethyl, isobutyl, isoanyl alcohols on their sodium derivatives"; Comptes Rendu Acad. Sci.; 1899; vol. 128; pp. 1002-1004.

Ndou et al.; "Dimerisation of ethanol to butanol over solid-base catalysts"; Applied Catalysis A: General; 251; 2003; pp. 337-345.

Reddy et al.; "A Single-step Synthesis of Isobutyraldehyde from Methanol and Ethanol over $CuO$—$ZnO$—$Al_2O_3$"; J. Chem. Soc., Chem. Commun.; 1992; pp. 997-998.

Reddy et al.; "Vapour Phase Synthesis of Isobutyraldehyde from Methanol and Ethanol over Mixed Oxide Supported Vanadium Oxide Catalysts"; Res. Chem. Intermed.; vol. 23; No. 8; 1997; pp. 703-713.

Shen et al.; "Vapor phase butanal self-condensation over unsupported and supported alkaline earth metal oxides"; Journal of Catalysis; 286; 2012; pp. 248-259.

Veibel et al.; "On the Mechanism of the Guerbet Reaction"; Tetrahedron; 1967; vol. 23; pp. 1723-1733.

Li et al.; "Synthesis of methacrolein by condensation of Propionaldehyde with formaldehyde"; Advanced Materials Research; vols. 396-398; pp. 1094-1097.

Zhong et al.; "Synthesis of Methacrolein"; Petrochemical Technology; 2011; vol. 40; No. 3; pp. 295-298 (Abstract Machine Translation).

Malinowski et al.; "Investigations into Aldol reactions During the Gaseious Phase III"; Roczniki Chemii : annals Societatis Chimicae Polonorum; 1957; 31; pp. 123-130.

Muhler, M.; "Oxidative Dehydrogenation of Alcohols to Aldehydes, Ketones, and Carboxylic Acids"; Handbook of Heterogeneous Catalysis; 1997; vol. 5; pp. 2274-2284.

Qian, et al.; "Formaldehyde synthesis from methanol over silver catalysts"; Applied Catalysis A: General; 238; 2003; pp. 211-222.

Ai, M.; "Formation of Acrylaldehyde by Vapor-Phase Aldol Condensation II. Phosphate Catalysts"; Bulletin of the Chemical Society of Japan; 1991; vol. 64; No. 4; pp. 1346-1350.

Notification of Transmittal of the International Search Report and the Written Opinion of the International Searching Authority dated Apr. 24, 2017 for International Application No. PCT/US2017/014818.

Notification of Transmittal of the International Search Report and the Written Opinion of the International Searching Authority dated May 1, 2017 for International Application No. PCT/US2017/014824.

Office Action dated Jun. 15, 2017 received in co-pending U.S. Appl. No. 15/008,833.

Notice of Allowance dated Oct. 12, 2017 received in co-pending U.S. Appl. No. 15/008,833.

* cited by examiner

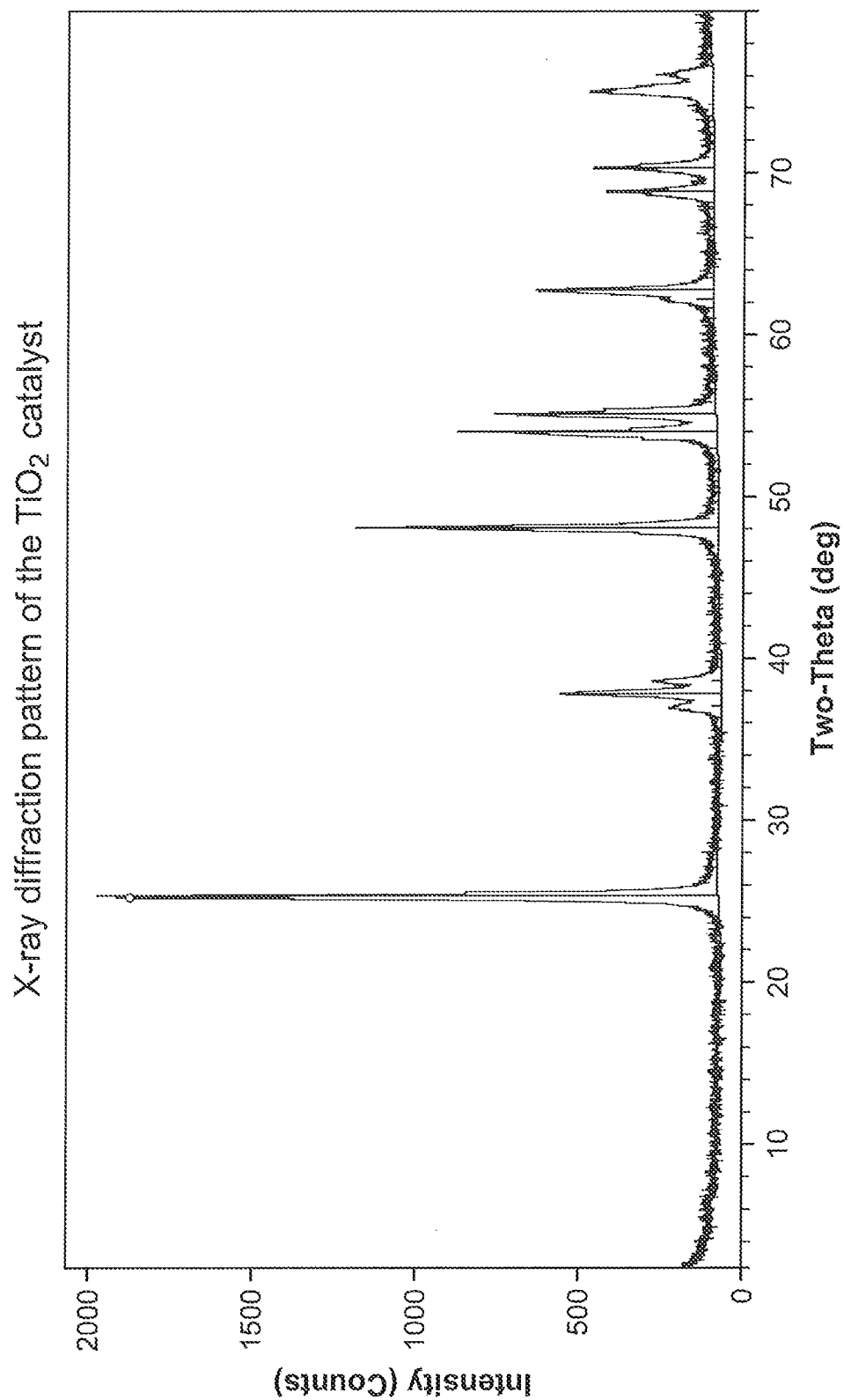

EFFICIENT SYNTHESIS OF METHACROELIN AND OTHER ALPHA, BETA-UNSATURATED ALDEHYDES OVER A REGENERABLE ANATASE TITANIA CATALYST

FIELD OF THE INVENTION

This invention generally relates to a process for the preparation of α,β-unsaturated aldehyde compounds using a heterogeneous anatase titania catalyst with an aldehyde and a formaldehyde source under vapor-phase condensation conditions to obtain an α,β-unsaturated aldehyde compound with high conversion and selectivity values.

BACKGROUND OF THE INVENTION

Methacrolein (or methacrylaldehyde) is an industrially useful chemical for the synthesis of a multitude of acrylate based polymers and resins. Among these applications, it is an intermediate for the production of methacrylonitrile and methacrylic acid. The latter is produced in an oxidation process and is a precursor for large scale applications such as methyl methacrylate and other esters.

The known process for methacrolein production involves the formation of propionaldehyde from ethylene hydroformylation (ethylene oxo) followed by the coupling of propionaldehyde with formaldehyde to form methacrolein. The yields for this synthetic approach are often greater than 95%. The major drawback of this process is that it requires a homogeneous Mannich base (typically a primary or a secondary amine) and an organic acid. While earlier patents detailed batch processes for the aldol reaction limiting their industrial applicability, latter patents revealed methods for a continuous process although the need for huge quantities of Mannich base and organic acid requires that the continuous process be run diluted at high atmospheric pressures. Although research in this area has developed the use of solid acid catalysts such as Amberlyst for the aldol condensation of formaldehyde and propionaldehyde, the process still requires one equivalent of a secondary amine. In many cases, this amine catalyst is consumed by the reaction which adds to the separation and feed costs.

The art additionally details various vapor-phase condensation reactions involving formaldehyde and other aldehydes or ketones over an unmodified silica gel catalyst. Although methacrolein was produced in some of this work, there are at least three technical requirements that limit the commercial ability of this process: 1) The ratios of the aldehyde to formaldehyde were not 1:1 and in many examples were as high as 20:1, thus increasing the feedstock costs, separation costs, or both; 2) The need for high temperatures for the condensation reaction, for example, the condensation of propionaldehyde and formaldehyde over the silica gel catalyst required temperatures in excess of 460° C.; and 3) Despite the high temperatures required to give appreciable amounts of methacrolein, the highest recorded conversions were only about 45%.

In an ideal methacrolein process, a continuous 1:1 reactant stream of only formaldehyde and propionaldehyde would be condensed together over a simple regenerable heterogeneous catalyst. This idealized process would aid downstream separations since the catalyst would not be part of the reactor effluent. Noting these advantages, research in developing this type of ideal process has progressed in the direction of designing an efficient heterogeneous catalyst. For example, the prior art teaches the synthesis of methacrolein from acetaldehyde or propionaldehyde and methanol over a $Bi_aMo_bX_cO_d$ catalyst (where, X=Al, Si, Ti, Fe, Co, Ag, W, V and/or P and a, b, c, d are the atomic ratios). Although these 3-metal catalysts had limited examples of acceptable runs with 86.6% selectivity at 67.5% conversion, the drawbacks for successful industrial implementation of this process include the synthesis of the complicated 3-metal catalyst along with the low yields obtained in all cases. Related catalyst work with borosilicate catalysts provided only low single pass yields of 56.6% with 57.5% conversion and 98% selectivity. Nearly 40% of the propionaldehyde used had to be recycled after each pass increasing separation volumes and costs. Similarly in other research, the aldol condensation of propionaldehyde and formaldehyde over a sodium oxide and silicic acid catalyst systems also showed poor yields of only 46%.

The present invention allows for the facile synthesis of methacrolein directly from the reaction of propionaldehyde and formaldehyde in the vapor-phase over an unmodified anatase titania catalyst. Moreover, it was surprisingly discovered that aldehydes such as methacrolein are unexpectedly stable over a titania catalyst given the potential for this molecule to undergo further aldol condensation and oligomerization. The present invention's use of a titania catalyst towards the synthesis of methacrolein and other α,β-unsaturated aldehyde compounds from a feed of the corresponding aldehyde and formaldehyde offer multiple advantages not previously addressed by the prior art. These advantages include: 1) improved aldol selectivity and conversion; 2) high single pass yields; 3) regenerable catalyst activity; 4) cleaner downstream separations due to the heterogeneous titania catalyst; and 5) efficient reactivity at atmospheric pressures.

SUMMARY OF THE INVENTION

The present invention provides in a first embodiment a process for preparing an α,β-unsaturated aldehyde compound, comprising: contacting a formaldehyde source, a diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

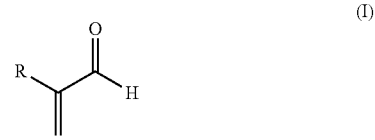

wherein R is a hydrogen or a hydrocarbon group having 1-12 carbons.

The present invention provides in a second embodiment a process for preparing methacrolein, comprising: contacting a formaldehyde source, a hydrogen containing diluent gas, and a propionaldehyde with a heterogeneous anatase titania catalyst under vapor-phase condensation conditions to obtain methacrolein; wherein methacrolein has the general formula (I):

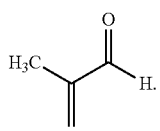

(II)

The present invention provides in a third embodiment a process for preparing an α,β-unsaturated aldehyde compound, comprising: contacting an aqueous formaldehyde source, a hydrogen containing diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

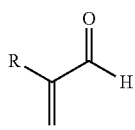

(I)

wherein R is a hydrogen or a hydrocarbon group having 1-12 carbons.

BRIEF DESCRIPTION OF THE DRAWINGS

FIG. 1 is an X-ray diffraction pattern of the titania ($TiO_2$) catalyst.

DETAILED DESCRIPTION OF THE INVENTION

It has been surprisingly discovered that the efficient and regenerable production of α,β-unsaturated aldehydes can be obtained over a commercially available titania catalyst from economically advantaged formaldehyde and the respective aldehyde feedstocks. One such example that works with this process is the production of methacrolein from formaldehyde and propionaldehyde. The major advantages of this invention are that the catalyst is readily available, non-toxic, and stable against consecutive aldol condensation reactions. The simplistic nature of anatase catalysts precludes the design and synthesis of complicated multi metal acid catalysts or homogeneous catalysts that typically increase downstream separation costs. The present invention is also advantageous as the aldol condensation of formaldehyde and propionaldehyde proceeds with highly reproducible yields over the titania catalyst and only a marginal drop in space time yields over the course of the reaction when hydrogen is used as a diluent gas.

The present invention provides in a first embodiment a process for preparing an α,β-unsaturated aldehyde compound, comprising: contacting a formaldehyde source, a diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

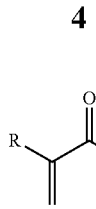

(I)

wherein R is a hydrogen or a hydrocarbon group having 1-12 carbons.

The formaldehyde source, diluent gas, and aldehyde are contacted in a reactor zone bearing the heterogeneous anatase titania condensation catalyst. The reaction zone can be oriented vertically or horizontally. For vertically oriented reactor zones, the vapor feed may enter at the bottom of the zone and move up the reactor or the vapor feed may enter at the top of the zone and move down the reactor. The type of reactor is not particularly limiting. Examples of suitable reactors include, but are not limited to, fixed bed reactors, fluidized bed reactors, tubular reactors, stirred tank reactors, Berty reactors, and the like.

The term, "formaldehyde", as used herein, represents the molecule HCHO and can be in a gaseous, aqueous, or anhydrous form. The formaldehyde source for use in the present invention is not particularly limiting. The formaldehyde source can also be 1,3,5-trioxane (sometimes referred to herein as simply "trioxane") or dimethoxymethane. Alternatively, the formaldehyde source may also be an aqueous solution of formaldehyde. The aqueous formaldehyde solution can contain, for example, from 30 to 65 weight percent formaldehyde, many of these commercial stock solutions are readily available. Examples of such solutions include Formalin (37 wt % formaldehyde in water which may contain up to 15% methanol) and industrial grade aqueous formaldehyde (55 wt % formaldehyde). The aqueous formaldehyde solution may be obtained commercially, by oxidation of methanol, or by heating water with trioxane, for example, in a molar ratio of approximately 4:1.

The formaldehyde source can be fed as anhydrous formaldehyde in the form of trioxane or paraformaldehyde dissolved in the aldehyde. The aqueous formaldehyde solution can be fed to the reaction zone separate from or as a mixture with the aldehyde. Feeding the formaldehyde and aldehyde to the reactor zone can occur in conjunction with a diluent gas.

The molar ratio of the formaldehyde to aldehyde reagents may be from 0.2 to 5, from 0.2 to 2, or 1 to 1. The molar ratio of water to the formaldehyde component may be from 0 to 5, from 0 to 3, or from 0 to 1.5.

The term, "diluent gas", as used herein, is a gas that is introduced with the reagent streams so that this gas quantitatively lowers the concentration of the reactants in feed. The composition of the "diluent gas" can comprise steam, methane, carbon dioxide, carbon monoxide, nitrogen, argon, oxygen, air, hydrogen, helium, or mixtures thereof. The molar ratio of the diluent gas to the total moles of reactant aldehydes can range from 0.01:1 to 20:1, 0.01:1 to 10:1, 0.01:1 to 5:1, 0.1:1 to 20:1, 0.1:1 to 10:1, or 0.1:1 to 1:1.

An additional aspect of the invention detailed herein is the utilization of hydrogen as a carrier gas. Typically, nitrogen or an inert gas is used as a carrier/diluent gas but the use of hydrogen unexpectedly increases the space time yields of methacrolein possibly due to the hydrogenation of inhibitory carbonaceous species.

In some embodiments of the process of the invention, the reactants can be fed to the reactor zone with hydrogen along with an inert carrier gas such as nitrogen or oxygen-depleted air. Gases recycled from the process can be used. The inert gas component can be present at concentrations ranging from 0 to 90 mole % of the total feed, from 25 to 85 mole %, or from 30 to 80 mole %. The concentration of the hydrogen gas component can range from 10 to 90 mole %, 15 to 75 mole %, 20 to 70 mole %, 0.5 to 6 mole %, from 2 to 5 mole %, or from 3 to 4 mole %. Oxygen can additionally be added to the diluent gas for the reaction since low levels or a lack of oxygen allow for coke to build up on the catalyst. On the other hand, high levels of oxygen can lead to excessive combustion of reactants and products. In some examples, the concentration of the oxygen component can be 0.5 to 6 mole %, from 2 to 5 mole %, or 3 to 4 mole %.

The space velocity for these condensation reactions should range from 50 to 400 moles of feed/(kg catalyst-hr), from 100 to 300 moles of feed/(kg catalyst-hr), or from 125 and 200 moles of feed/(kg catalyst-hr). The term "moles of feed" is meant to be inclusive of all of the species being fed to the catalyst including organics, solvents, and diluent gases. These embodiments of the invention take advantage of the combined effects of feeding the correct levels of reagents, diluent gases, water, and elevated space velocity to increase rate and selectivity without significantly affecting the yield. Any differences in formaldehyde conversion are primarily the result of formaldehyde destruction when the space velocity is too low. In the event of inhibitory coke formation, the catalyst may be regenerated between reaction runs in air at, for example, 400° C.

Generally, increasing the space velocity of reactants increases the rate of a reaction, but this is normally accompanied with a corresponding decrease in the yield and conversion. It has been unexpectedly discovered that certain conditions of the process can actually allow for increased rate without a decrease in yield as the space velocity is increased.

The term, "aldehyde", as used herein, represents the broad class of organic compounds having the generic formula RCHO, and characterized by an unsaturated carbonyl functionality (C=O). Other than formaldehyde, which will be referred to specifically in this specification, aldehyde will refer to a molecule having at least 2 hydrogen atoms in the alpha position to the aldehyde carbonyl group which will form the alkene or double bonded carbon added through the formaldehyde in the aldol condensation reaction.

The aldehyde has at least 2 hydrogen atoms in the position alpha to the aldehyde carbonyl group as shown below:

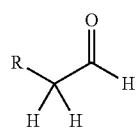

(i)

The aldehyde is fed to the reactor zone comprising a heterogeneous anatase titania condensation catalyst and contacted with a formaldehyde source. The aldehyde can be any aldehyde wherein R is a hydrogen or a hydrocarbon group having 1 to 12 carbon atoms amenable to aldol condensation reactions. For example, this aldehyde comprises acetaldehyde, propionaldehyde, n-butyraldehyde, pentanal, hexanal, heptanal, octanal, nonanal, decanal, undecanal, dodecanal, 3-methylbutyraldehyde, 3-ethylbutyraldehyde and 3-ethylpentanal, but-3-enal, pent-3-enal, 2-cyclohexylacetaldehyde, 2-phenylacetaldehyde, or a combination thereof. In some examples, the aldehyde can be a linear saturated aldehyde such as acetaldehyde, propionaldehyde, n-butyraldehyde, pentanal, hexanal, heptanal, octanal, nonanal, decanal, undecanal, dodecanal, or a combination thereof. In other examples, the aldehyde can be a branched saturated aldehyde comprising 3-methylbutyraldehyde, 3-ethylbutyraldehyde, 3-ethylpentanal, or a combination thereof. In yet other examples, the aldehyde can be unsaturated non-conjugated aldehydes comprising but-3-enal, pent-3-enal, or combinations thereof. In another set of examples, the aldehyde can have cyclic or aromatic substituents and comprise 2-cyclohexylacetaldehyde, 2-phenylacetaldehyde, or combinations thereof. Heteroatom functional groups such as alcohols, ethers, esters, amines, amides, thiols, and halogens may also be present as substituents in the aldehyde in some examples.

In some examples, the aldehyde can be an aldehyde wherein R is a hydrocarbon group having 1-2, 1-3, 1-4, 1-5, 1-6, 1-7, 1-8, 2-3, 2-4, 2-5, 2-6, 2-7, 2-8, 3-4, 3-5, 3-6, 3-7, 3-8, 3-9, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, 9-10, 9-11, or 10-12 carbon atoms.

The heterogeneous anatase titania catalyst comprises titanium dioxide, titanium IV oxide, titania, or $TiO_2$. Each of these titanium dioxide, titanium IV oxide, titania, and $TiO_2$ materials may exist and can be used in the anatase, rutile, and brookite mineral forms although the anatase polymorph of titania is the crystalline phase found to be active towards the formaldehyde and aldehyde condensation reaction. In some embodiments, the titanium dioxide, titanium IV oxide, titania, and $TiO_2$ materials are used entirely in the anatase form. In other embodiments, the titanium dioxide, titanium IV oxide, titania, and $TiO_2$ materials are used as a mixture of the anatase and rutile forms. In some embodiments, the heterogeneous titania catalyst is used in the anatase mineral form. The titania catalyst should be physically robust and pre-shaped. The term "pre-shaped" is used in this context to mean that the shape of the final catalyst is essentially the same as the starting material. The titania catalyst typically can have average particle diameter sizes ranging from about 0.1 millimeter (mm) to about 20 mm. The catalyst can be in any common form such as extrudates, compressed pellets, or bulk solid that has been pulverized to the desired mesh size. They may also be in a variety of shapes such as rods, stars, cylinders, spheres, or broken chunks. Many of these anatase titania catalysts are available commercially, and their use simplifies the preparation of the catalyst composition of the invention, although this is not a requirement of the invention.

The reactions described herein are vapor-phase reactions catalyzed by heterogeneous aldol condensation catalysts. The term "heterogeneous aldol condensation catalyst", as used herein, refers to a solid catalyst useful in the aldol condensation of lower aldehydes to higher aldehydes. The term "vapor-phase", as used herein, refers to reactor conditions wherein the feed aldehydes and ensuing products are above their dew point. Dew point is defined as the temperature below which liquid condensation takes place from a gaseous mixture having a condensable material at a given pressure.

Vapor-phase condensation conditions are the temperature and pressure parameters that promote the chemical reaction of formaldehyde with the aldehyde in the gaseous state to form α,β-unsaturated compounds with the loss of a water molecule. The temperature used for the vapor-phase condensation is between about 100° C. and about 500° C., between about 100° C. and about 350° C., and between about 100° C. and about 300° C. In some embodiments, the condensation reaction is performed at a temperature of 250° C., 290° C., or 320° C. The reaction is normally run between 0.1 and 10.0 bars absolute (bara), between 0.5 and 5.0 bara, or at atmospheric pressure.

The condensation reaction described herein produces α,β-unsaturated aldehydes from the aldol condensation of formaldehyde with an aldehyde. The α,β-unsaturated aldehydes produced through this reaction have the general formula:

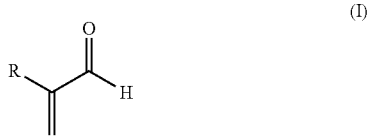

(I)

in which the aldehydic C=O function is conjugated to an unsaturated C—C bond at the alpha, beta positions and wherein the R group is a hydrogen or a hydrocarbon group having 1-12 carbons. The R group can be an alkyl, aryl, alkoxy, or aryloxy group. These α,β-unsaturated aldehydes may also be referred to as α-substituted acrolein compounds or 2-methylene substituted aldehydes. As previously described, in addition to formaldehyde, the aldehyde fed to the reactor zone with a heterogeneous anatase titania catalyst can be any primary aldehyde comprising 2 to 12 carbon atoms amenable to aldol condensation reactions. The α,β-unsaturated aldehyde compounds synthesized from the reaction of formaldehyde with an aldehyde are acrolein (2-methyleneethanal), methacrolein (2-methylenepropanal), 2-methylenebutanal, 2-methylenepentanal, 2-methylenehexanal, 2-methyleneheptanal, 2-methyleneoctanal, 2-methylenenonanal, 2-methylenedecanal, 2-methyleneundecanal, 2-methylenedodecanal, 3-methyl-2-methylenebutanal, 3-methyl-2-methylenepentanal, 3-ethyl-2-methylenepentanal, 2-methylenebut-3-enal, 2-methylenepent-3-enal, 2-cyclohexylacrylaldehyde, or 2-phenylacrylaldehyde. Heteroatom functional groups such as alcohols, ethers, esters, amines, amides, thiols and halogens may also be present as substituents in the α,β-unsaturated aldehyde depending on the aldehyde used.

In some examples, the α,β-unsaturated aldehyde can have the general formula (I) wherein R is a hydrocarbon group having 1-2. 1-3, 1-4, 1-5, 1-6, 1-7, 1-8, 2-3, 2-4, 2-5, 2-6, 2-7, 2-8, 3-4, 3-5, 3-6, 3-7, 3-8, 3-9, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, 9-10, 9-11, or 10-12 carbon atoms.

The α,β-unsaturated aldehydes can be prepared with good yield, conversion, and selectivity. The term "yield", as used herein, is meant to be the (moles of product)/(moles of reactant fed)*100. For example, the percent yield of methacrolein from formaldehyde is the (moles of methacrolein)/(moles of formaldehyde fed)*100. The term "conversion", as used herein, is meant to be the (moles of reactant fed−moles of unreacted reactant)/(moles of reactant fed)*100. For example, the percent formaldehyde conversion is (moles of formaldehyde fed−moles of unreacted formaldehyde)/(moles of formaldehyde fed)*100. The term "selectivity", as used herein, is meant to be (moles of product)/(moles of reactant fed−moles of unreacted reactant)*100. For example, the percent selectivity to methacrolein from formaldehyde is (moles of methacrolein)/(moles of formaldehyde fed−moles of unreacted formaldehyde)*100. One skilled in the art recognizes that yield is also equal to conversion times selectivity. When comparing examples, such as, Example B having an 80% formaldehyde conversion and Example C having a 60% formaldehyde conversion, the formaldehyde conversion of Example B is said to be 20% higher than Example C. In other words, comparisons are simply the mathematical difference in the percentages from one example to another.

Inhibitors such as hydroquinone may be added to the α,β-unsaturated aldehyde product to minimize oligomerization or polymerization.

The aldehyde conversion in the vapor-phase condensation reaction of a formaldehyde source, a diluent gas, and an aldehyde is greater than 80%. The aldehyde conversion in the vapor-phase condensation reaction of a formaldehyde source, a diluent gas, and an aldehyde is greater than 70%, greater than 75%, greater than 80%, greater than 85%, or greater than 90%. At 290° C., using 8/14 mesh heterogeneous anatase titania catalyst, the aldehyde conversion in the vapor-phase condensation reaction of a formaldehyde source, a diluent gas, and an aldehyde is greater than 80%, greater than 85%, or greater than 90%. At 310° C., using 8/14 mesh heterogeneous anatase titania catalyst, the aldehyde conversion in the vapor-phase condensation reaction of a formaldehyde source, a diluent gas, and an aldehyde is greater than 80%, or greater than 85%.

The α,β-unsaturated aldehyde selectivity in the vapor-phase condensation reaction of a formaldehyde source, a diluent gas, and an aldehyde is greater than 70%, greater than 75%, greater than 80%, or greater than 85%. The α,β-unsaturated aldehyde selectivity in the vapor-phase condensation reaction of a formaldehyde source, a diluent gas, and an aldehyde is greater than 70%, greater than 75%, greater than 80%, greater than 85%, or greater than 90%. At 290° C., using 8/14 mesh heterogeneous anatase titania catalyst, the α,β-unsaturated aldehyde selectivity in the vapor-phase condensation reaction of a formaldehyde source, a diluent gas, and an aldehyde is greater than 80%, or greater than 85%. At 310° C., using 8/14 mesh heterogeneous anatase titania catalyst, the α,β-unsaturated aldehyde selectivity in the vapor-phase condensation reaction of a formaldehyde source, a diluent gas, and an aldehyde is greater than 75%, greater than 80%, or greater than 85%.

The α,β-unsaturated aldehyde space time yield (STY) in the vapor-phase condensation reaction of a formaldehyde source, a diluent gas, and an aldehyde is 8.0, 8.5, or 9.0 moles of α,β-unsaturated aldehyde/(kg catalyst-hr). The α,β-unsaturated aldehyde space time yield in the vapor-phase condensation reaction of a formaldehyde source, a diluent gas, and an aldehyde is 7.5, 8.0, 8.5, 9.0, 9.5, or 10.0 moles of α,β-unsaturated aldehyde/(kg catalyst-hr). At 290° C., using 8/14 mesh heterogeneous anatase titania catalyst, the α,β-unsaturated aldehydes space time yield in the vapor-phase condensation reaction of a formaldehyde source, a diluent gas, and an aldehyde is 10.0 moles of α,β-unsaturated aldehyde/(kg catalyst-hr). At 310° C., using 8/14 mesh heterogeneous anatase titania catalyst, the α,β-unsaturated aldehyde space time yield in the vapor-phase condensation reaction of a formaldehyde source, a diluent gas, and an aldehyde is 8.5, or 9.0 moles of α,β-unsaturated aldehyde/ (kg catalyst-hr).

In the event of inhibitory coke formation on the heterogeneous anatase titania catalyst, the catalyst may be regenerated between reaction runs in air at 450° C.

Many uses exist for methacrolein and the other α,β-unsaturated aldehydes described herein such as for the synthesis of a multitude of acrylate based polymers and resins. For example, methacrolein can be used to produce or synthesize isobutyraldehyde, methacrylonitrile, methacrylic acid, and methyl methacrylate as monomers or other reagent chemicals. In industrial applications, methacrolein can be used to synthesize or produce methacrylic acid through an oxidation process; this methacrylic acid can then be esterified to synthesize or produce methyl methacrylate and/or a variety other methacrylate esters. The methyl methacrylate synthesized from methacrolein can be polymerized or copolymerized to produce polymethyl methacrylate (PMMA) or copolymers of PMMA, or a combination thereof. The other types of methacrylate esters synthesized from methacrolein can be polymerized or copolymerized to produce homopolymers of the methacrylate ester or esters used, copolymers of the methacrylate ester or esters used, or a combinations thereof. Methocrolein can be used to synthesize or produce methacrylonitrile; this methacrylonitrile can then be used to make homopolymers, copolymers, or elastomers of polymethacrylonitrile. In some examples, methocrolein can be used to synthesize or produce isobutyraldehyde.

The present invention provides in a second embodiment a process for preparing methacrolein, comprising: contacting a formaldehyde source, a hydrogen containing diluent gas, and a propionaldehyde with a heterogeneous anatase titania catalyst under vapor-phase condensation conditions to obtain methacrolein; wherein methacrolein has the general formula (I):

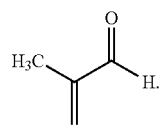

(II)

It is understood that the descriptions outlining and teaching the method for preparing α,β-unsaturated aldehydes previously discussed, which can be used in any combination, apply equally well to the second embodiment of the invention, where applicable, disclosing a process for preparing methacrolein.

The formaldehyde source, hydrogen containing diluent gas, and a propionaldehyde are contacted in a reactor zone bearing the heterogeneous anatase titania condensation catalyst. The type of reactor is not particularly limiting. Examples of suitable reactors include, but are not limited to, fixed bed reactors, fluidized bed reactors, tubular reactors, stirred tank reactors, Berty reactors, and the like.

The formaldehyde source for use in the present invention is not particularly limiting. The formaldehyde source can be in a gaseous, aqueous, or anhydrous form such as trioxane or paraformaldehyde dissolved in the aldehyde. The aqueous formaldehyde solution can be fed to the reaction zone separate from or as a mixture with the aldehyde. Feeding the formaldehyde and propionaldehyde to the reactor zone can occur in conjunction with a hydrogen containing diluent gas.

The molar ratio of the formaldehyde to propionaldehyde reagents may be from 0.2 to 5, from 0.2 to 2, or 1 to 1. The molar ratio of water to the formaldehyde component may be from 0 to 5, from 0 to 3, or from 0 to 1.5.

The term, "hydrogen containing diluent gas", as used herein, is a gas that contains at least some hydrogen gas that is introduced with the reagent streams so that this gas quantitatively lowers the concentration of the reactants in the feed. The composition of the "hydrogen containing diluent gas" has at least some hydrogen gas and may additionally comprise steam, methane, carbon dioxide, carbon monoxide, nitrogen, argon, oxygen, air, helium, or mixtures thereof. The molar ratio of the hydrogen containing diluent gas to the total moles of reactant propionaldehyde can range from 0.01:1 to 20:1, 0.01:1 to 10:1, 0.01:1 to 5:1, 0.1:1 to 20:1, 0.1:1 to 10:1, or 0.1:1 to 1:1. In some embodiments, nitrogen or an inert gas is used as part of the hydrogen containing diluent gas because the use of hydrogen unexpectedly increases the space time yields of methacrolein possibly due to the hydrogenation of inhibitory carbonaceous species.

In some embodiments of the invention, the formaldehyde and propionaldehyde can be fed to the reactor zone with hydrogen along with an inert carrier gas such as nitrogen or oxygen-depleted air. Gases recycled from the process can be used. The inert gas component can be present at concentrations ranging from 0 to 90 mole % of the total feed, from 25 to 85 mole %, or from 30 to 80 mole %. The concentration of the hydrogen gas component can range from 10 to 90 mole %, 15 to 75 mole %, 20 to 70 mole %, 0.5 to 6 mole %, from 2 to 5 mole %, or from 3 to 4 mole %.

In other embodiments, oxygen can additionally be added to the hydrogen containing diluent gas with the reactants since low levels or a lack of oxygen allow for coke to build up on the catalyst. On the other hand, high levels of oxygen can lead to excessive combustion of reactants and products. In some examples, the concentration of the oxygen component can be 0.5 to 6 mole %, from 2 to 5 mole %, or 3 to 4 mole %.

The space velocity for these condensation reactions should range from 50 to 400 moles of feed/(kg catalyst-hr), from 100 to 300 moles of feed/(kg catalyst-hr), or from 125 and 200 moles of feed/(kg catalyst-hr). The term "moles of feed" is meant to be inclusive of all of the species being fed to the catalyst including organics, solvents, and diluent gases. These embodiments of the invention take advantage of the combined effects of feeding the correct levels of reagents, diluent gases, water, and elevated space velocity to increase rate and selectivity without significantly affecting the yield. Any differences in formaldehyde conversion are primarily the result of formaldehyde destruction when the space velocity is too low. In the event of inhibitory coke formation, the catalyst may be regenerated between reaction runs in air at, for example, 450° C.

The propionaldehyde has 2 hydrogen atoms in the position alpha to the aldehyde carbonyl group as shown below:

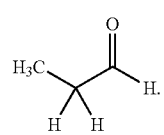

(ii)

The propionaldehyde is fed to the reactor zone comprising a heterogeneous anatase titania condensation catalyst and contacted with a formaldehyde source.

The heterogeneous anatase titania catalyst comprises titanium dioxide, titanium IV oxide, titania, or $TiO_2$. In some embodiments, the heterogeneous titania catalyst is used in the anatase mineral form. The titania catalyst should be physically robust and pre-shaped. The term "pre-shaped" is used in this context to mean that the shape of the final catalyst is essentially the same as the starting material. The titania catalyst typically can have average particle diameter sizes ranging from about 0.1 millimeter (mm) to about 20 mm. The catalyst can be in any common form such as extrudates, compressed pellets, or bulk solid that has been pulverized to the desired mesh size. They may also be in a variety of shapes such as rods, stars, cylinders, spheres, or broken chunks. Many of these anatase titania catalysts are available commercially, and their use simplifies the preparation of the catalyst composition of the invention, although this is not a requirement of the invention.

Vapor-phase condensation conditions are the temperature and pressure parameters that promote the chemical reaction of formaldehyde with the propionaldehyde in the gaseous state to form methacrolein with the loss of a water molecule. The temperature used for the vapor-phase condensation is between about 100° C. and about 500° C., between about 100° C. and about 350° C., and between about 100° C. and about 300° C. In some embodiments, the condensation reaction is performed at a temperature of 250° C., 290° C., or 320° C. The reaction is normally run between 0.1 and 10.0 bars absolute (bara), between 0.5 and 5.0 bara, or at atmospheric pressure.

The condensation reaction described herein with propionaldehyde as the reagent produces methacrolein from the aldol condensation of formaldehyde and propionaldehyde. The α,β-unsaturated aldehydes produced through this reaction have the general formula:

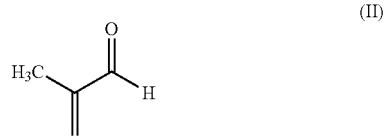

(II)

in which the aldehydic C=O function is conjugated to an unsaturated C—C bond at the alpha, beta positions.

The methacrolein can be prepared with good yield, conversion, and selectivity. The term "yield", as used herein, is meant to be the (moles of product)/(moles of reactant fed)*100. For example, the percent yield of methacrolein from formaldehyde is the (moles of methacrolein)/(moles of formaldehyde fed)*100. The term "conversion", as used herein, is meant to be the (moles of reactant fed−moles of unreacted reactant)/(moles of reactant fed)*100. For example, the percent formaldehyde conversion is (moles of formaldehyde fed−moles of unreacted formaldehyde)/(moles of formaldehyde fed)*100. The term "selectivity", as used herein, is meant to be (moles of product)/(moles of reactant fed−moles of unreacted reactant)*100. For example, the percent selectivity to methacrolein from formaldehyde is (moles of methacrolein)/(moles of formaldehyde fed−moles of unreacted formaldehyde)*100. One skilled in the art recognizes that yield is also equal to conversion times selectivity. When comparing examples, such as, Example B having an 80% formaldehyde conversion and Example C having a 60% formaldehyde conversion, the formaldehyde conversion of Example B is said to be 20% higher than Example C. In other words, comparisons are simply the mathematical difference in the percentages from one example to another.

Inhibitors such as hydroquinone may be added to the methacrolein product to minimize oligomerization and polymerization products.

The propionaldehyde conversion in the vapor-phase condensation reaction of a formaldehyde source, a hydrogen containing diluent gas, and an aldehyde is greater than 80%. The propionaldehyde conversion in the vapor-phase condensation reaction of a formaldehyde source, a hydrogen containing diluent gas, and propionaldehyde is greater than 70%, greater than 75%, greater than 80%, greater than 85%, or greater than 90%. At 290° C., using 8/14 mesh heterogeneous anatase titania catalyst, the propionaldehyde conversion in the vapor-phase condensation reaction of a formaldehyde source, a hydrogen containing diluent gas, and propionaldehyde is greater than 80%, greater than 85%, or greater than 90%. At 310° C., using 8/14 mesh heterogeneous anatase titania catalyst, the propionaldehyde conversion in the vapor-phase condensation reaction of a formaldehyde source, a hydrogen containing diluent gas, and propionaldehyde is greater than 80%, or greater than 85%.

The methacrolein selectivity in the vapor-phase condensation reaction of a formaldehyde source, a hydrogen containing diluent gas, and propionaldehyde is greater than 70%, greater than 75%, greater than 80%, or greater than 85%. The methacrolein selectivity in the vapor-phase condensation reaction of a formaldehyde source, a hydrogen containing diluent gas, and propionaldehyde is greater than 70%, greater than 75%, greater than 80%, greater than 85%, or greater than 90%. At 290° C., using 8/14 mesh heterogeneous anatase titania catalyst, the methacrolein selectivity in the vapor-phase condensation reaction of a formaldehyde source, a hydrogen containing diluent gas, and propionaldehyde is greater than 80%, or greater than 85%. At 310° C., using 8/14 mesh heterogeneous anatase titania catalyst, the methacrolein selectivity in the vapor-phase condensation reaction of a formaldehyde source, a hydrogen containing diluent gas, and propionaldehyde is greater than 75%, greater than 80%, or greater than 85%.

The methacrolein space time yield (STY) in the vapor-phase condensation reaction of a formaldehyde source, a hydrogen containing diluent gas, and propionaldehyde is 8.0, 8.5, or 9.0 moles of methacrolein/(kg catalyst-hr). The methacrolein space time yield in the vapor-phase condensation reaction of a formaldehyde source, a hydrogen containing diluent gas, and propionaldehyde is 7.5, 8.0, 8.5, 9.0, 9.5, or 10.0 moles of methacrolein/(kg catalyst-hr). At 290° C., using 8/14 mesh heterogeneous anatase titania catalyst, the methacrolein space time yield in the vapor-phase condensation reaction of a formaldehyde source, a hydrogen containing diluent gas, and propionaldehyde is 10.0 moles of α,β-unsaturated aldehyde/(kg catalyst-hr). At 310° C., using 8/14 mesh heterogeneous anatase titania catalyst, the methacrolein space time yield in the vapor-phase condensation reaction of a formaldehyde source, a hydrogen containing diluent gas, and propionaldehyde is 8.5, or 9.0 moles of methacrolein/(kg catalyst-hr).

In the event of inhibitory coke formation on the heterogeneous anatase titania catalyst, the catalyst may be regenerated between reaction runs in air at 450° C.

The present invention provides in a third embodiment a process for preparing an α,β-unsaturated aldehyde compound, comprising: contacting an aqueous formaldehyde source, a hydrogen containing diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

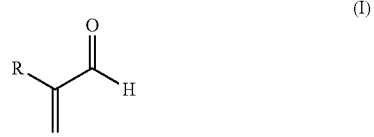

(I)

wherein R is a hydrogen or a hydrocarbon group having 1-12 carbons.

It is understood that the descriptions outlining and teaching the method for preparing α,β-unsaturated aldehydes, including methacrolein, previously discussed, which can be used in any combination, apply equally well to the third embodiment of the invention, where applicable, disclosing a process for preparing α,β-unsaturated aldehydes.

There are also many different variations on the composition elements, reductants, reaction conditions, and reactants used that could be employed and would be obvious to one skilled in the art.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used in the specification and claims, the singular forms "a," "an," and "the" include their plural referents unless the context clearly dictates otherwise. For example, a reference to "a catalyst" or "a reductant" is synonymous with "at least one" or "one or more" catalysts or reductants and is thus intended to refer to both a single or a plurality of catalysts or reductants. In addition, references to a composition containing or including "an" ingredient is intended to include other ingredients or elements in addition to the one named.

The terms "containing" or "including" are intended to be synonymous with the word "comprising," meaning that at least the named compound, element, particle, or method step, etc., is present in the composition or article or method, but does not exclude the presence of other compounds, catalysts, materials, particles, method steps, etc., even if such compounds, materials, particles, method steps, etc., have the same function as what is named, unless expressly excluded in the claim.

Listing of Non-Limiting Embodiments

Embodiment A is a process for preparing an α,β-unsaturated aldehyde compound, comprising: contacting a formaldehyde source, a diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

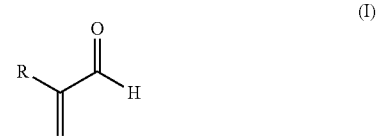

wherein R is a hydrogen or a hydrocarbon group having 1-12 carbons.

The process of Embodiment A, wherein the formaldehyde source and the aldehyde are contacted with the heterogeneous anatase titania catalyst at a temperature of about 100° C. to about 500° C.

The process of Embodiment A or Embodiment A with one or more of the intervening features wherein the formaldehyde source and the aldehyde are contacted with the heterogeneous anatase titania catalyst at a temperature of about 100° C. to about 300° C.

The process of Embodiment A or Embodiment A with one or more of the intervening features wherein the diluent gas comprises nitrogen, hydrogen, air, or a combination thereof.

The process of Embodiment A or Embodiment A with one or more of the intervening features wherein the formaldehyde source comprises trioxane, formaldehyde, formalin, or a combination thereof.

The process of Embodiment A or Embodiment A with one or more of the intervening features wherein the aldehyde comprises acetaldehyde, propionaldehyde, n-butyraldehyde, pentanal, hexanal, heptanal, octanal, nonanal, decanal, undecanal, dodecanal, 3-methylbutyraldehyde, 3-ethylbutyraldehyde and 3-ethylpentanal, but-3-enal, pent-3-enal, 2-cyclohexylacetaldehyde, 2-phenylacetaldehyde, or a combination thereof.

The process of Embodiment A or Embodiment A with one or more of the intervening features wherein the aldehyde is a linear saturated aldehyde comprising acetaldehyde, propionaldehyde, n-butyraldehyde, pentanal, hexanal, heptanal, octanal, nonanal, decanal, undecanal, dodecanal, or a combination thereof.

The process of Embodiment A or Embodiment A with one or more of the intervening features wherein the aldehyde is a branched saturated aldehyde comprising 3-methylbutyraldehyde, 3-ethylbutyraldehyde and 3-ethylpentanal, or a combination thereof.

The process of Embodiment A or Embodiment A with one or more of the intervening features wherein the aldehyde is a cyclic or an aromatic substituted aldehyde comprising 2-cyclohexylacetaldehyde, 2-phenylacetaldehyde, or a combination thereof.

The process of Embodiment A or Embodiment A with one or more of the intervening features wherein the heterogeneous anatase titania catalyst is regenerated with a calcination step at 450° C. in air.

The process of Embodiment A or Embodiment A with one or more of the intervening features wherein the α,β-unsaturated aldehyde compound is produced with a conversion and a selectivity above 80%.

The process of Embodiment A or Embodiment A with one or more of the intervening features wherein the α,β-unsaturated aldehyde compound is produced with a space time yield greater than 8 moles aldehyde/kg catalyst/hr.

Embodiment B is a process for preparing methacrolein, comprising: contacting a formaldehyde source, a hydrogen containing diluent gas, and a propionaldehyde with a heterogeneous anatase titania catalyst under vapor-phase condensation conditions to obtain methacrolein; wherein methacrolein has the general formula (I):

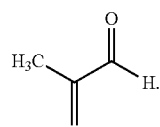

(II)

The process of Embodiment B wherein the formaldehyde source comprises trioxane, formaldehyde, formalin, or a combination thereof.

The process of Embodiment B or Embodiment B with one or more of the intervening features wherein the α,β-unsaturated aldehyde compound is produced with a conversion and a selectivity above 80%.

The process of Embodiment B or Embodiment B with one or more of the intervening features wherein the α,β-unsaturated aldehyde compound is produced with a space time yield greater than 8 moles aldehyde/kg catalyst/hr.

The process of Embodiment B or Embodiment B with one or more of the intervening features wherein the methacrolein is used to produce isobutyraldehyde, methacrylonitrile, methacrylic acid, methyl methacrylate, poly(methyl methacrylate), or a combination thereof.

Embodiment C is a process for preparing an α,β-unsaturated aldehyde compound, comprising: contacting an aqueous formaldehyde source, a hydrogen containing diluent gas, and an aldehyde with a heterogeneous anatase titania catalyst under vapor-phase condensation conditions to obtain the α,β-unsaturated aldehyde compound; wherein the α,β-unsaturated aldehyde compound has the general formula (I):

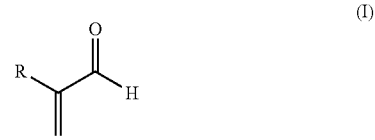

(I)

wherein R is a hydrogen or a hydrocarbon group having 1-12 carbons.

The process of Embodiment C wherein the α,β-unsaturated aldehyde compound is produced with a conversion and a selectivity above 80%.

The process of Embodiment C or Embodiment C with one or more of the intervening features wherein the α,β-unsaturated aldehyde compound is produced with a space time yield greater than 8 moles aldehyde/kg catalyst/hr.

EXAMPLES

Materials

The trioxane, propionaldehyde, anatase titania catalyst, solvents, additional reagents, and gases were purchased from commercial suppliers and used as received. The titania catalyst's crystal structure was determined using X-ray diffraction and was noted to be the pure anatase polymorph of $TiO_2$ as shown in FIG. 1. The surface area of the catalyst was 36.8 m²/g as calculated by the Brunnauer, Emmett and Teller (BET) theory using nitrogen gas as the adsorbent. The pore volume and pore diameter of the catalyst as determined from $N_2$ physisorption measurements was found to be 0.14 cm³/g and 150 Å respectively.

XRD Measurements

All XRD measurements were performed on a Rigaku Miniflex X-Ray Diffraction Spectrometer using a Copper anode X-Ray tube operated at 30 kV and 15 mA. Diffraction patterns were collected from 5 degree two theta angle to 75 degree two theta angle with a sampling width of 0.02 degrees and a scan speed of 1.00 degrees/min.

Crystallite size was calculated based on the measurement of the full width half maximum for peaks in the diffraction pattern and use of the Scherrer equation (P. N. Scherrer, *Ges. Wiss. Gottingen, Math.—Phys.* Kl. 2, 96-100 (1918)). Quantitative phase analysis was calculated using a refinement algorithm base on the Rietveld method (H. M. Rietveld, *J. Applied Crystallography* 21, 86-91 (1988)). Percent crystallinity was calculated based on integrated intensities from the individual diffraction patterns with peaks of crystallite size greater than 30 Å defined as crystalline and peaks of crystallite size less than or equal to 30 Å defined as amorphous (N. S. Murthy et al., *Polymers* 31, 996-1002 (1990)).

Gas Chromatography Measurements

Liquid product samples were collected over a measured time period, weighed and analyzed by gas chromatography.

THF was added to the products to homogenize the organic and the water layers. Samples were weighed into a gas chromatography (GC) vial to a recorded weight of 0.1XXX g (where X is the actual number shown on the balance). Initially a stock ISTD solution comprising 75 g of cyclohexanone in acetonitrile was made-up. To 1.0XX g of the THF homogenized reaction product, approximately 7.86XX gram of ISTD solution was added. The vial was then capped and gently mixed. The contents were then transferred into a 2-mL GC vial. The vials were then placed on a heat plate at 80° C. for 30 minutes. To separate the components, each sample was injected on two BD-Wax/DB-1301 columns (60 m×0.32 mm×1.00 μm) running in parallel at 40° C. on a Shimadzu 2010 gas chromatograph with an AOC-20 autosampler. The concentration of propionaldehyde, methacrolein, water, iso-butyraldehyde and other analytes were detected using this approach using the TCD and/or FID detectors.

Examples 1-2: Methacrolein Production Using $TiO_2$ Catalyst (in 3.2 mm Pellets Form) from Propionaldehyde and Formaldehyde in Nitrogen Flow Reaction:

The vapor-phase condensation reactions of formaldehyde (as trioxane) with propionaldehyde were performed at temperatures ranging from 290° C. to 310° C., using a 0.2 mL liquid feed/minute for 4 or 6 hours. The residence time was maintained constant at approximately 1 second by changing the diluent $N_2$ gas flow rate. The performance of the catalyst is summarized in performance Table 1. The conversions presented in Table 1 are based on moles of propionaldehyde converted to initial moles of propionaldehyde and the space time yield (STY) of acrylic acid is equal to the moles of methacrolein produced per kg of catalyst per hour. The selectivities are based on the final moles of methacrolein relative to the reacted moles of propionaldehyde. The reacted moles of propionaldehyde are the difference between the initial and final moles of propionaldehyde. The yield percentage detailed in the introduction is the product of the conversion and selectivity.

The vapor-phase condensation reaction of formaldehyde (fed as trioxane) with propionaldehyde was performed in a 25 mm outer diameter (21 mm inner diameter) quartz reactor tube with length=79 cm (31 inches). Heat to the reactor was provided by an Applied Test Systems series 3210 three element electric furnace having a heated zone 54 cm (21.25 inches) in length. Liquid products were collected in a three necked flask fitted with a glycol chilled (0° C.) jacket and an additional dry ice trap. The third neck of the flask was connected to a side arm which was connected to a dry ice trap. The base of the main receiver flask and dry ice trap were fitted with a stopcock to allow for draining of the liquid products.

The quartz reactor had indentations 16 cm (6.25 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 8 inches in height above the indentations to allow the catalyst to be positioned in the middle of the 3 element furnace. The reactor was then loaded with an approximately 10.0 mL charge of catalyst. The three point thermocouple in the thermowell was placed 1.5 inches up from the base of the catalyst bed. Sufficient quartz chips were added to the region above the catalyst charge to reach the top of the heated region of the 3 element furnace. Liquid samples were collected over a measured time period, weighed and analyzed by gas chromatography.

As a substantial exotherm was observed in the first 3 to 10 minutes of the reaction, the sample collected during the first hour of reaction was discarded. The reaction activities and yields presented in Table 1 were collected over a period of 2 to 4 hours after the initial 1 hour temperature stabilization period. The residence time for the reaction was kept constant at approximately 1 second by varying the nitrogen gas flow rate. The catalyst was regenerated at 450° C. in air overnight.

TABLE 1

Methacrolein production from condensation of formaldehyde (HFr) and propionaldehyde (HPr) using nitrogen as a carrier gas - $TiO_2$ Catalyst was 3.2 mm pellets

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 1 | 1/1 | 310 | 2 | 81 | 81 | 8.8 |
|   |     |     | 4 | 74 | 82 | 8.2 |
| 2 | 1/1 | 290 | 2 | 87 | 72 | 8.4 |
|   |     |     | 4 | 79 | 85 | 9.1 |

Table 1 illustrates that the efficient synthesis of methacrolein from formaldehyde and propionaldehyde can be obtained over an unmodified commercially available titania catalyst.

Examples 3-4: Methacrolein Production Using $TiO_2$ Catalyst (in 3.2 mm Pellets Form) from Propionaldehyde and Formaldehyde in Hydrogen Flow Examples 3-4 were conducted as described above in Examples 1 and 2 except that the diluent gas was changed from nitrogen to hydrogen. The results are presented below in Table 2.

TABLE 2

Methacrolein production from condensation of formaldehyde (HFr)
and propionaldehyde (HPr) using hydrogen as a carrier gas - TiO$_2$ Catalyst
was 3.2 mm pellets

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 3 | 1/1 | 310 | 2 | 85 | 79 | 9 |
|   |     |     | 4 | 74 | 89 | 8.9 |
| 4 | 1/1 | 290 | 2 | 87 | 78 | 9.1 |
|   |     |     | 4 | 79 | 89 | 9.5 |

Comparing the results in Tables 1 and 2, the space time yields are higher when the diluent gas is hydrogen compared with an inert gas like nitrogen. This increased yield could be attributed to less coke formation on the catalyst due to the hydrogenation of inhibitory carbonaceous species. Less catalyst coking could potentially lead to an increase in the catalytically active sites resulting in higher space time yields of methacrolein. When the diluent gas used was hydrogen, the space time yields increased or remained constant with reaction time unlike when nitrogen was used as the carrier gas, wherein the space time yields dropped as the reaction time was increased from 2 hours to 4 hours (at 310° C.). To further illustrate the importance of hydrogen, the following experiments were conducted.

Examples 5-6: Methacrolein Production Using TiO$_2$ Catalyst (in 8/14 Mesh Form) from Propionaldehyde and Formaldehyde in Nitrogen Flow Examples 5-6 were conducted as described above in Examples 1 and 2 except the catalyst used had smaller particle size. To mitigate mass transfer effects of the catalyst and to illustrate the importance of hydrogen, the anatase TiO$_2$ catalyst was crushed and sieved into 8/14 mesh sized particles which were used as the catalyst material for this set of experiments. The results are presented below in Table 3.

TABLE 3

Methacrolein production from condensation of formaldehyde (HFr)
and propionaldehyde (HPr) using nitrogen as a carrier gas - TiO$_2$ Catalyst
was 8/14 mesh sized particles

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 5 | 1/1 | 310 | 2 | 82 | 70 | 7.7 |
|   |     |     | 4 | 74 | 84 | 8.4 |
| 6 | 1/1 | 290 | 2 | 92 | 76 | 9.4 |
|   |     |     | 4 | 86 | 87 | 10.1 |

Examples 7-8: Methacrolein Production Using TiO$_2$ Catalyst (in 8/14 Mesh Form) from Propionaldehyde and Formaldehyde in Hydrogen Flow Examples 7-8 were conducted as described above in Examples 5 and 6 except that the diluent gas was changed from nitrogen to hydrogen. The catalyst used was anatase TiO$_2$ catalyst in the form of 8/14 mesh sized particles. The results are presented below in Table 4.

TABLE 4

Methacrolein production from condensation of formaldehyde (HFr)
and propionaldehyde (HPr) using hydrogen as a carrier gas - TiO$_2$ Catalyst
was 8/14 mesh sized particles

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 7 | 1/1 | 310 | 2 | 86 | 75 | 8.8 |
|   |     |     | 4 | 80 | 85 | 9.1 |
| 8 | 1/1 | 290 | 2 | 91 | 81 | 10.0 |
|   |     |     | 4 | 86 | 87 | 10.1 |

Tables 2 and 4 demonstrate that higher space time yields were obtained in the presence of hydrogen as a carrier gas. The use of hydrogen is an unexpected aspect of this invention since most condensation experiments are conducted in the presence of nitrogen or an equivalent inert gas.

Example 9: Reproducibility of Example 8 and Longer Term Stability of the Catalyst Experiment 9 was conducted as described above in Examples 7-8 with a hydrogen flow. Prior experiments demonstrated that 290° C. is a more optimal operating temperature than 310° C. since the space time yields were higher at the former temperature. Therefore, the longer term stability test was conducted at 290° C. The experiment was continued for 2 more hours to analyze a longer reaction window to determine stability of the catalyst. The results are presented below in Table 5.

TABLE 5

Methacrolein production from condensation of formaldehyde (HFr) and propionaldehyde (HPr) using hydrogen as a carrier gas - $TiO_2$ Catalyst was 8/14 mesh sized particles

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 9 | 1/1 | 290 | 2 | 91 | 82 | 10.0 |
|   |     |     | 4 | 86 | 88 | 10.2 |
|   |     |     | 6 | 80 | 92 | 9.9 |

The methacrolein production reaction was performed in accordance to conditions presented in Example 8 in Table 4. The catalyst was regenerated overnight at 450° C. in a continuous flow of 100 standard cubic centimeters per minute (SCCM) air. Comparing Examples 8 and 9 in Tables 4 and 5 above, the catalyst activity is completely reproducible after the regeneration step in air. For example, after 4 hours of reaction, the same propionaldehyde conversion (80%) was observed and the space time yields of methacrolein were almost the same as those presented in the earlier Example 8 at approximately 10.15 moles/kg catalyst/hr. These results highlight the stability of the catalyst. Furthermore, Example 9 shows that the drop in space time yields over 6 hours is only 3% (from 10.2 units to 9.9 units). These Examples highlight the importance of using hydrogen as a carrier gas and is further corroborated by Example 10.

Example 10: Reproducibility of Example 9

Example 10 was conducted as described above in Example 9 with a hydrogen flow. As presented in Table 6, the catalytic activity is highly reproducible and the catalyst is completely regenerable upon a calcination step in air at 450° C.

TABLE 6

Methacrolein production from condensation of formaldehyde (HFr) and propionaldehyde (HPr) using hydrogen as a carrier gas - $TiO_2$ Catalyst was 8/14 mesh sized particles

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 10 | 1/1 | 290 | 2 | 92 | 81 | 10.0 |
|    |     |     | 4 | 87 | 85 | 10.0 |
|    |     |     | 6 | 78 | 92 | 9.7 |

Examples 11-12: Methacrolein Production Using TiO$_2$ Catalyst (in 8/14 Mesh Form) from Propionaldehyde and Formaldehyde in Hydrogen Flow in the Presence of Water Examples 11-12 were carried out with an anatase titania catalyst. The earlier experiments were conducted with trioxane (containing 0% water) as the source of formaldehyde while the most commonly available grade of formaldehyde is approximately 55% by weight in water. To simulate this, appropriate amounts of water were added to a solution of 1/1 formaldehyde (trioxane) and propionaldehyde to simulate a formaldehyde solution containing approximately 55% by weight water. As displayed in Table 7, only a small drop of 5% in space time yields was observed at 290° C. This suggests that the catalytic reaction to methacrolein proceeds efficiently over the titania catalyst in the presence of water.

TABLE 7

Methacrolein production from condensation of formaldehyde (HFr) and propionaldehyde (HPr) using hydrogen as a carrier gas - TiO$_2$ Catalyst was 8/14 mesh sized particles in the presence of water

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 11 | 1/1 | 310 | 2 | 81 | 84 | 8.4 |
|  |  |  | 4 | 74 | 86 | 7.9 |
| 12 | 1/1 | 290 | 2 | 88 | 87 | 9.5 |
|  |  |  | 4 | 83 | 94 | 9.6 |

Example 13-15: Additional Examples with Other Titania Sources

Examples 13-15 were carried out with an anatase titania catalyst. In these examples the residence time was maintained at approximately 0.6 seconds by varying the diluent nitrogen gas flowrate.

TABLE 8

Methacrolein production from condensation of formaldehyde (HFr) and propionaldehyde (HPr) using nitrogen as a carrier gas - TiO$_2$ Catalyst was 8/14 mesh sized particles

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 13 | 1/1 | 325 | 4 | 49 | 77 | 9.6 |
| 14 | 1/1 | 300 | 4 | 55 | 80 | 11.2 |
| 15 | 1/1 | 275 | 4 | 49 | 79 | 9.9 |

Example 16: Application of Rutile TiO$_2$

The Examples performed above were all carried out with titania obtained from multiple sources but each sample consisted of the anatase polymorph as the major crystalline phase. To broaden the use of any titania as a potential catalyst, the following examples are catalyzed with a rutile polymorph of titania purchased from a commercial source. In Example 16, the residence time was maintained at approximately 1 second by varying the diluent nitrogen gas flowrate. As can be seen from Table 9 below, rutile titania was determined to not perform as well as the anatase polymorph of TiO$_2$.

TABLE 9

Methacrolein production from condensation of formaldehyde (HFr) and propionaldehyde (HPr) with hydrogen as a carrier gas using the rutile form of titania as the catalyst

| Example | HPr/HFr | Furnace Temp (° C.) | Reaction Time (hrs) | HPr Conversion (%) | Methacrolein Selectivity (%) | Methacrolein STY (moles/kg catalyst/hr) |
|---|---|---|---|---|---|---|
| 16 | 1/1 | 290 | 2 | 35 | 69 | 3.0 |
|  |  |  | 4 | 22 | 87 | 2.4 |

We claim:

1. A process for preparing an α,β-unsaturated aldehyde compound, comprising:
    contacting a formaldehyde source, a hydrogen containing diluent gas, and an aldehyde with a heterogeneous anatase titania catalyst under vapor-phase condensation conditions to obtain the α,β-unsaturated aldehyde compound;
    wherein the α,β-unsaturated aldehyde compound has the general formula (I):

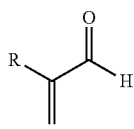

(I)

wherein R is a hydrogen or a hydrocarbon group having 1-12 carbons wherein the molar ratio of the formaldehyde to aldehyde reagents is from 0.2 to 5.

2. The process according to claim 1, wherein the formaldehyde source and the aldehyde are contacted with the heterogeneous anatase titania catalyst at a temperature of about 100° C. to about 500° C.

3. The process according to claim 1, wherein the formaldehyde source and the aldehyde are contacted with the heterogeneous anatase titania catalyst at a temperature of about 100° C. to about 300° C.

4. The process according to claim 1, wherein the formaldehyde source comprises trioxane, formaldehyde, formalin, or a combination thereof.

5. The process of claim 1, wherein the aldehyde comprises acetaldehyde, propionaldehyde, n-butyraldehyde, pentanal, hexanal, heptanal, octanal, nonanal, decanal, undecanal, dodecanal, 3-methylbutyraldehyde, 3-ethylbutyraldehyde and 3-ethylpentanal, but-3-enal, pent-3-enal, 2-cyclohexylacetaldehyde, 2-phenylacetaldehyde, or a combination thereof.

6. The process according to claim 1, wherein the aldehyde is a linear saturated aldehyde comprising acetaldehyde, propionaldehyde, n-butyraldehyde, pentanal, hexanal, heptanal, octanal, nonanal, decanal, undecanal, dodecanal, or a combination thereof.

7. The process according to claim 1, wherein the aldehyde is a branched saturated aldehyde comprising 3-methylbutyraldehyde, 3-ethylbutyraldehyde and 3-ethylpentanal, or a combination thereof.

8. The process according to claim 1, wherein the aldehyde is a cyclic or an aromatic substituted aldehyde comprising 2-cyclohexylacetaldehyde, 2-phenylacetaldehyde, or a combination thereof.

9. The process according to claim 1, wherein the heterogeneous anatase titania catalyst is regenerated with a calcination step at 450° C. in air.

10. The process according to claim 1, wherein the α,β-unsaturated aldehyde compound is produced with a space time yield greater than 8 moles aldehyde/kg catalyst/hr.

11. A process for preparing methacrolein, comprising:
    contacting a formaldehyde source, a hydrogen containing diluent gas, and a propionaldehyde with a heterogeneous anatase titania catalyst under vapor-phase condensation conditions to obtain methacrolein;
    wherein methacrolein has the general formula (I):

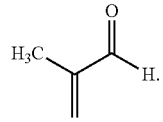

(II)

12. The process according to claim 11, wherein the formaldehyde source comprises trioxane, formaldehyde, formalin, or a combination thereof.

13. The process according to claim 11, wherein the methacrolein is produced with a space time yield greater than 8 moles methacrolein/kg catalyst/hr.

14. The process according to claim 11, wherein the methacrolein is used to produce isobutyraldehyde, methacrylonitrile, methacrylic acid, methyl methacrylate, poly(methyl methacrylate), or a combination thereof.

15. A process for preparing an α,β-unsaturated aldehyde compound, comprising:
    contacting an aqueous formaldehyde source, a hydrogen containing diluent gas, and an aldehyde with a heterogeneous anatase titania catalyst under vapor-phase condensation conditions to obtain the α,β-unsaturated aldehyde compound;
    wherein the α,β-unsaturated aldehyde compound has the general formula (I):

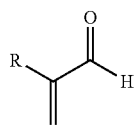

(I)

wherein R is a hydrogen or a hydrocarbon group having 1-12 carbons; wherein the molar ratio of the formaldehyde to aldehyde reagents is from 0.2 to 5.

16. The process according to claim 15, wherein the α,β-unsaturated aldehyde compound is produced with a space time yield greater than 8 moles aldehyde/kg catalyst/hr.

17. The process according to claim 11, wherein the concentration of hydrogen in the diluent gas is within a range of 10 to 90 mole %.

18. The process according to claim 15, wherein the concentration of hydrogen in the diluent gas is within a range of 10 to 90 mole %.

* * * * *